United States Patent [19]

Cesa et al.

[11] Patent Number: 4,749,786

[45] Date of Patent: * Jun. 7, 1988

[54] α-AMINO ACIDS THROUGH CATALYTIC REACTION OF CO AND A HYDROXYL COMPOUND WITH ENAMIDES

[75] Inventors: Mark C. Cesa, South Euclid; James D. Burrington, Richmond Heights, both of Ohio

[73] Assignee: The Standard Oil Company, Cleveland, Ohio

[*] Notice: The portion of the term of this patent subsequent to Dec. 1, 2004 has been disclaimed.

[21] Appl. No.: 34,517

[22] Filed: Apr. 6, 1987

Related U.S. Application Data

[63] Continuation-in-part of Ser. No. 552,561, Nov. 16, 1983, Pat. No. 4,710,574.

[51] Int. Cl.$^4$ .................. C07D 225/02; C07D 223/06

[52] U.S. Cl. ..................... 540/450; 540/480; 540/596; 540/603; 540/607; 546/201; 546/210; 546/245; 548/336; 548/344; 548/532; 548/533; 548/535; 548/466; 548/496; 548/497

[58] Field of Search ............... 548/533, 344, 496, 497, 548/535, 532, 336, 466; 546/201, 210, 245; 540/450, 480, 596, 603, 607

[56] References Cited

PUBLICATIONS

Barton, J. in *Protective Groups in Organic Chemistry*, J. McOmie (Editor), Plenum Press, London, 1973, pp. 46–49.

*Primary Examiner*—Richard A. Schwartz
*Attorney, Agent, or Firm*—C. S. Lynch; D. J. Untener; L. W. Evans

[57] ABSTRACT

Disclosed is the hydrocarboxylation of defined enamides with CO and a compound ROH to make amido acids or amido esters, either of which can be hydrolyzed to α-amino acids.

2 Claims, No Drawings

α-AMINO ACIDS THROUGH CATALYTIC REACTION OF CO AND A HYDROXYL COMPOUND WITH ENAMIDES

This is a continuation-in-part of application Ser. No. 552,561, filed Nov. 16, 1983, now U.S. Pat. No. 4,710,574.

This invention relates to making α-amino acids through catalytic reaction of CO and a hydroxyl compound with enamides.

In the publication by Y. Becker, A. Eisenstadt and J. K. Stille at pages 2145-2151 of J. Org. Chem., Volume 45 (1980), it is disclosed that enamides when reacted with methanol in the presence of CO under hydrocarboxylation conditions do not result in hydrocarboxylation, the only reaction being addition of methanol across the double bond, even though certain enimides were successfully hydrocarboxylated.

We have found the contrary to be true, that the enamides can be hydrocarboxylated and that this is an important route to produce α-amino acids.

It is an object of the invention to make α-amino acids or their precursors through addition of CO and a hydroxyl compound across the double bond of an enamide.

Other objects, as well as features, aspects and advantages, of the invention will be apparent from a study of the specification, including the specific examples and the claims.

According to the present invention there is provided a process for making α-amino acids which comprises hydrolyzing the product made by reacting an enamide with water or an organic hydroxyl compound according to the equation

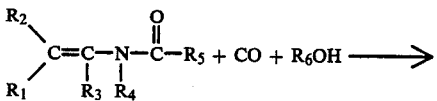

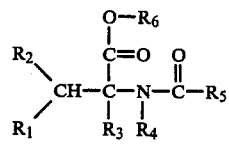

wherein each of $R_1$, $R_2$, $R_3$, $R_4$, $R_5$ and $R_6$ contain no ethylenic or acetylenic unsaturation, contain zero to 15 carbon atoms and are independently selected from:
(1) H or a hydrocarbyl group,
(2) a hydrocarbyl group substituted with acylamino, acyl-(N-hydrocarbyl) amino, formylamino and formyl-(N-hydrocarbyl) amino, hydrocarbyloxy, hydrocarbylthio, acyloxy, acylthio, carboxyl, hydrocarbyl carboxyl, hydrocarbyl thiocarboxyl, hydrocarbyl amino, dihydrocarbyl amino, hydrocarbonyl, hydrocarbyl carbonyl, 3-indolyl, carbamoyl, hydrocarbylcarbamoyl, dihydrocarbylcarbamoyl, 5-imidazolyl, 2-guanidinoyl and halo groups, and wherein
(3) $R_1$ and $R_2$ can additionally be selected independently from acylamino, acyl-(N-hydrocarbyl) amino, formylamino and formyl-(N-hydrocarbyl) amino, hydrocarbyloxy, hydrocarbylthio, hydrocarbyl amino, dihydrocarbyl amino, acyloxy, acylthio, carboxyl, hydrocarbyl carboxyl, hydrocarbyl thiocarboxyl, hydrocarbonyl, hydrocarbyl carbonyl, 3-indolyl, carbamoyl, hydrocarbylcarbamoyl, dihydrocarbylcarbamoyl, 5-imidazolyl, 2-guanidinoyl and halo groups, and wherein $R_6$ can additionally be a hydrocarbyl group having one or more hydroxy substituents, and
wherein $R_1$ and $R_2$, $R_1$ and $R_3$, or $R_2$ and $R_3$ can be linked to form or complete a ring, and wherein $R_4$ can be linked with $R_1$ or $R_2$ to form or complete a ring. In an especially useful embodiment $R_4$ is linked with $R_1$ or $R_2$ to form or complete a ring; usually in such event each of $R_4$ and the linked $R_1$ or $R_2$ independently contains 1 to 4 C atoms.

The present invention is of considerable value in the making of amino acids occurring in nature and analagous compounds, and derivatives thereof. With the exception of methionine and glycine, amino acids occurring in nature are produced by extraction from plant or animal sources or by microbial and enzymatic fermentation. The biocatalytic routes suffer from some serious drawbacks. They are quite slow, require rigidly controlled and highly dilute reaction conditions, and often produce a mixture of products from which isolation and purification of the desired amino acid is laborious and expensive. Methionine and glycine are currently made by HCN based non-catalytic routes. Chemical syntheses of amino acids by current methods require expensive and toxic HCN.

The novel process of the present invention produces α-carboxy amides as shown in the foregoing equation. In the second step of the invention the products of the first step are hydrolyzed to α-amino acids of the invention, as follows:

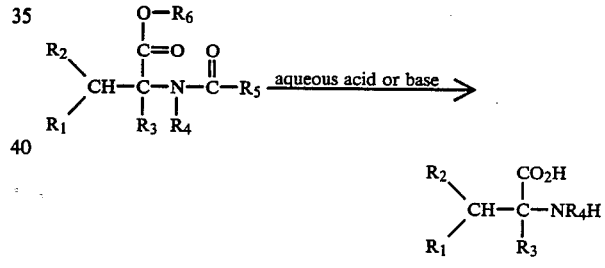

where $R_1$, $R_2$, $R_3$ and $R_4$ in the α-amino acid hydrolysis product are the same as in the starting material or may contain hydroxyl, thiol, carboxylic acid, thiocarboxylic acid or amine groups as a result of the hydrolysis of functional groups contained in one or more of the $R_1$, $R_2$, $R_3$ and $R_4$ radicals of the starting material.

It should be noted that, when making α-amino acids, for instance, phenylalanine, according to the two step method of the present invention, $R_6$ is usually hydrocarbyl or a hydrocarbyl saturated monohydric aliphatic alcohol containing only C, H and O.

The hydrocarboxylation products are all useful to make the α-amino acids according to the present invention. The amino acids are all useful to make peptides by known methods, and these can be converted to proteins to make animal feed supplements, for instance. The amino acids can also be converted to useful solid polyamides by conventional condensation techniques, useful for thermoplastic molding of solid shapes, such as structural parts, plates, tumblers, etc.

The hydrocarboxylation reaction is carried out catalytically and can be effected continuously or in a batch operation in the liquid phase, or in the vapor phase where feasible at the reaction temperatures noted hereafter. Usually it is effected in a batch operation in a solvent under pressure.

The reactant concentration may vary widely and are not critical. For convenience, the ratio of the hydrocarboxylation reactant $R_6OH$ to the enamide should be no greater than 100/1 on a molar basis and is preferably at least 1/1. The amount of carbon monoxide can vary widely, but it is usual to carry out the reaction under a carbon monoxide pressure of zero to 3500 psig, more usually 250 to 2500 psig. The amount of catalyst can also vary widely. Most conveniently, the amount of catalyst is between 0.001 and 100 mole percent based on the enamide, more usually 0.1 to 10 mole percent.

Usually, the reaction is carried out with a solvent. The solvent should be inert under the reaction conditions and preferably dissolve the active catalyst species as well as the reactants but not necessarily all of the CO. Suitable solvents found to date include tetrahydrofuran, benzene, $CH_3CN$ and $CH_2Cl_2$, $CHCl_3$, $CCl_4$, toluene, ethyl ether and dimethylformamide. The now preferred solvent is tetrahydrofuran, particularly when using $(\phi_3P)_2PdCl_2$ catalyst, or other palladium compounds. Usually, the amount of solvent in the system will be such that the enamide concentration is at least about 0.01 weight percent in the solution, but not over 70 weight percent.

The reaction is normally carried out at a temperature of 0° to 250° C., preferably 20° to 150° C. However, the reaction temperature can be below or above this if desired. Reaction times on the order of 0.1 to 250 hours can be employed, with reaction times on the order of 2 to 100 hours being more convenient.

While a wide variety of complexes of transition metals are known as catalysts for the hydrocarboxylation of alkenes (See, for instance, 1) Pino, P., Piacenti, F., in *Organic Synthesis via Metal Carbonyls*, Volume 2, Wender, I., Pino, P., eds., Wiley, New York, 1977, pp. 233–296; 2) Falbe, J., New Syntheses with Carbon Monoxide, New York, Springer Verlag, Chapter 3 and 5; 3) Forster, D.; Hershman, A.; Morris, D. E., *Catal. Rev.-Sci. Eng.* 23, 89–105 (1981); 4) Parshall, G. W., *Catal. Rev. Sci-Eng.*, 23, 107–124 (1981); 5) Bittler, J, v. Kutepow, N., Neubauer, D., reis, H., *Angew. Chem. Intl. Ed.* Eng., 7, 329–335 (1968)), but no reference known suggests that enamides can be hydrocarboxylated. Indeed, the cited Becker et al. reference teaches that hydrocarboxylation does not work with enamides, the exclusive reaction being the addition of methanol across the double bond. Catalyst useful are generally transition metal catalyst compounds, particularly coordination complexes of such metals. Palladium coordination complexes are effective, especially those complexed with phosphine such as $P_3$. However, many known transition metal catalyst complexes for hydrocarboxylation of alkenes, or for hydroformylation for enol ethers or enol acetates (U.S. Pat. No. 3,888,880; B. Fell, M. Barl, *J. Mol. Catal.*, 1977, 2, 301–6; Tinker, Harold B. (Monsanto) Ger. Offen. No. 2,623,673; U.S. Pat. No. 4,072,709) are not effective in the present hydrocarboxylation. Especially useful Pd complexes are $(\phi_3P)_2PdCl_2$ and $(3P)_4Pd$ with HCl as a co-catalyst. When $(\phi_3P)_2PdCl_2$ is the catalyst, the now preferred reaction solvent is tetrahydrofuran.

Once the hydrocarboxylation reaction is completed, the product amido acid or ester can be recovered from the reaction system in a conventional manner, such as for example, by vacuum distillation or crystallization.

The second step is a conventional hydrolysis reaction. It is catalyzed by any dilute aqueous acid or base. Suitable acids or bases are HCl, $H_2SO_4$, $HNO_3$, $H_3PO_4$, acetic acid, KOH, NaOH and $NH_4OH$. The reaction is conveniently carried out at temperatures at above 0° C. to 250° C., more usually about 20° to 150° C. If desired, water or non-interfering hydrophilic solvents can be used. Such solvents include tetrahydrofuran, $CH_3CN$, and the like. Reaction times on the order of 0.1 to 50 hours, usually 0.2 to 5 hours, can be employed.

The above hydrocarboxylation and hydrolysis provides a simple and straightforward system for producing amino acids using enamides as the starting material. As can be seen, it totally avoids the use of expensive HCN and the handling problems associated therewith.

The α-amino acids of the present invention have numerous uses. The naturally occurring amino acids have known uses. The phenylalanine product can be used in a known manner to make the sweetener aspartame. See U.S. Pat. No. 3,492,131, issued Jan. 27, 1970.

The following examples are merely illustrative and are not to be considered as limiting.

EXAMPLE 1

A 70 mL stainless steel high pressure reactor having a Pyrex glass liner and a magnetic stir bar was charged with 5 mL of tetrahydrofuran, 0.5 mmol of m-xylene internal standard, 2.5 mmol of methanol, 36 mg. of $(P\phi_3)_2PdCl_2$ and 0.5 mmol of 98.5 percent purity N-β-styrylbenzamide, and was pressurized to 1000 psig with CO at room temperature. This reaction mixture was stirred for 48 hours at 100° C. Thereafter, the reaction was cooled to room temperature and vented to atmospheric pressure. The reactor product was analyzed by gas chromatography and mass spectrometry and the analysis indicated a 77 percent conversion of the styrylbenzamide and a 15 percent selectivity to N-benzoylphenylalanine methyl ester. This product is hydrolyzable in acid or base to phenylalanine.

EXAMPLE 2

2.2 mmols of N-benzoylphenylalanine methyl ester was hydrolyzed by stirring with refluxing 2N HCl for 18 hours. The resulting product mixture was filtered to give a white solid, m.p. about 260° C. (49.2 mg). This product was shown by nmr spectroscopy to be phenylalanine with only a trace of benzoic acid.

EXAMPLE 3

A 70 mL stainless steel high pressure reactor having a Pyrex glass liner and a magnetic stir bar was charged with 5 mL of tetrahydrofuran, 0.5 mmol of m-xylene internal standard, 0.5 mmol of methanol, 37.3 mg. of $PdCl_2(P\phi_3)$ and 0.507 mmol of N-β-styrylacetamide, and was pressurized to 1000 psig with CO at room temperature. This reaction mixture was stirred for 48 hours at 100° C. Thereafter, the reaction was cooled to room temperature and vented to atmospheric pressure. The reaction product was analyzed by gas chromatography and mass spectrometry and the analysis indicated a 75.6 percent conversion of the styrylacetamide and a 18.3 percent selectivity to N-acetylphenylalanine methyl ester. This compound is hydrolyzable to phenylalanine.

EXAMPLE 4

A 70 mL stainless steel high pressure reactor having a Pyrex glass liner and a magnetic stir bar was charged with 5 mL of tetrahydrofuran, 5 mmol of m-xylene internal standard, 0.618 mmol of methanol, 38 mg. of (Pφ3)2PdCl2 and 0.565 mmol of 98.5 percent purity of N-β-strylbenzamide, and was pressurized to 1000 psig with CO at room temperature. This reaction mixture was stirred for 48 hours at 100° C. Thereafter, the reaction was cooled to room temperature and vented to atmospheric pressure. The reactor product was analyzed by gas chromatography and mass spectrometry and the analysis indicated a 76 percent conversion of the styrylacetamide and a 19.6 percent selectivity to N-benzoylphenylalanine methyl ester.

EXAMPLE 5

A 70 mL stainless steel high pressure reactor having a Pyrex glass liner and a magnetic stir bar was charged with 5 mL of tetrahydrofuran, 0.5 mmol of m-xylene internal standard, 0.6 mmol of methanol, 34.9 mg of (Pφ3)2PdCl2 and 0.5 mmol of N-vinylacetamide and was pressurized to 1000 psig with CO at room temperature. This reaction mixture was stirred for 24 hours at 100 C. Thereafter, the reaction was cooled to room temperature and vented to atmospheric pressure. The reactor product was analyzed by gas chromatography and mass spectrometry and the analysis indicated the presence of methyl 2-acetamido propionate. This product is hydrolyzable to alanine.

EXAMPLE 6

A 70 mL stainless steel high pressure reactor having a Pyrex glass liner and a magnetic stir bar was charged with 5 mL of tetrahydrofuran, 0.5 mmol of m-xylene internal standard, 0.6 mmol of methanol, 34.7 mg of (Pφ3)2PdCl2 and 0.5 mmol of 1-benzoylamino-2-methylpropene and was pressurized to 1000 psig with CO at room temperature. This reaction mixture was stirred for 24 hours at 100° C. Thereafter, the reaction was cooled to room temperature and vented to atmospheric pressure. The reactor product was analyzed by gas chromatography and mass spectrometry and the analysis indicated the presence of methyl benzoylamino-3-methyl butyrate. This product is hydrolyzable to valine.

EXAMPLES 7 TO 28

In the following examples 7 to 28 the enamides shown in the left column of Table 1 are reacted exactly as given in Example 1, but substituting the respective enamide mole for mole for the N-β-styrylbenzamide of that example, the other reactants and the conditions of time, temperature, CO pressure, catalyst and mole ratios being the same. The hydrocarboxylation reaction in each instance produces the compounds shown in the middle column. Each of the hydrocarboxylation reaction products of the middle column are thereafter hydrolyzed as in Example 2 to give the respective product α-amino acid shown in the right column.

In general, starting material enamides can be prepared by reacting the corresponding aldehyde and the corresponding amide to form an ethylidenebisamide which is then converted to the enamide by thermolysis. See R. Giger and D. Ben Ishai, Isr. J. Chem. 5, 253–9 (1967), incorporated herein by reference.

For instance, the enamide for Example 1 was so prepared, by reacting phenylacetaldehyde and benzamide to make 0.28 g. of β-phenylethylidinebisbenzamide. This was heated in a sublimator to 265° C. at 10 mm Hg for 25 minutes. A yellow-white solid (0.21 g.) was deposited in the coldfinger and was collected by careful scraping. Five additional runs were made and the crude yellow-white solids combined with the 0.21 g. from the first run. The combined crude products were recrystalized from ethanol-water to yield a pale yellow solid which was shown by NMR spectroscopy to be a 6.6/91.9 mixture of cis- and trans-N-β-styrylbenzamide of 98.5 percent purity (0.97 g., 52 percent yield) M.P. 161-164 C.

Other methods for marking enamides are shown in Hickmott, Tetrahedron, 38, No. 14, pp. 1975 to 2050, 1982; in Lenz, Synthesis, pp. 489–518, 1978; and in the book *The Chemistry of Amides* edited by Zabicky, Interscience Publishers, New York, 1970. All of the foregoing are incorporated herein by reference.

As will be evident to those skilled in the art various modifications of this invention can be made or followed in the light of the foregoing disclosure and discussion without departing from the spirit and scope of the disclosure of from the scope of the claims.

TABLE I

| Example No. | Enamide Reactant | Hydrocarboxylation Product | α-Amino Acid |
| --- | --- | --- | --- |
| 7 | N—vinylacetamide | methyl 2-acetamido propionate | alanine |
| 8 | 1-acetamido-2-methylpropene | methyl 2-acetamido-3-methyl butyrate | valine |
| 9 | 1-acetamido-3-methyl-1-butene | methyl 2-acetamido-4-methyl valerate | leucine |
| 10 | 1-acetamido-2-methyl-1-butene | methyl 2-acetamido-3-methyl valerate | isoleucine |
| 11 | 1-acetyl-2,3-dihydro-1H-pyrrole | 1-acetyl-2-methoxycarbonylpyrrolidine | proline |
| 12 | 1-(3-indolyl)-2-acetamidoethene | methyl 2-acetamido-3-(3-indolyl) propionate | tryptophan |
| 13 | 1-acetamido-3-methylthiopropene | methyl 2-acetamido-4-methylthio butyrate | methionine |
| 14 | 1-acetamido-2-acetyloxyethene | methyl 2-acetamido-3-acetyloxy propionate | serine |
| 15 | 1-acetamido-2-acetyloxypropene | methyl 2-acetamido-3-acetyloxy butyrate | threonine |
| 16 | 1-acetamido-2-acetylthioethene | methyl 2-acetamido-3-acetylthio propionate | cysteine |
| 17 | N—(4-acetoxystyryl)acetamide | methyl 2-acetamido-3-(4-acetyloxyphenyl)-propionate | tyrosine |
| 18 | N—(3,4-diacetoxystyryl)acetamide | methyl 2-acetamido-3-(3,4-diacetyloxyphenyl) | 2-amino-3-(dihydroxyphenyl)propionic acid |
| 19 | 3-acetamidoacrylamide | methyl 2-acetamido succinamate | asparagine |
| 20 | 4-acetamido-3-butenamide | methyl 2-acetamido glutaramate | glutamine |
| 21 | methyl-3-acetamidoacrylate | dimethyl 2-acetamido succinate | aspartic acid |
| 22 | methyl-4-acetamido-3-butenoate | dimethyl 2-acetamido glutarate | glutamic acid |
| 23 | 1,5-diacetamido-1-pentene | methyl 2,6-acetmido caproate | lysine |
| 24 | 1-acetamido-4-guanidinyl-1-butene | methyl 2-acetamido-5-guanidinyl valerate | arginine |
| 25 | 1-(5-imidazolyl)-2-acetamidoethene | methyl 2-acetamido-3-(5-imidazolyl)propionate | histidine |
| 26 | methyl (2-methoxycarbonyl-3-acetamido)-acrylate | dimethyl 2-acetamido-3-methoxycarbonyl | β-carboxyaspartic acid |
| 27 | 3-acetamido acrylic acid | methyl 2-acetamido succinic acid | aspartic acid |

TABLE I-continued

| Example No. | Enamide Reactant | Hydrocarboxylation Product | α-Amino Acid |
|---|---|---|---|
| 28 | N—(4-acetyloxy-3,5-dibromostyryl) acetamide | methyl 2-acetamido-3-(4-acetyloxy-3,5-dibromophenyl propionate | dibromotyrosine |

EXAMPLE 29

A 70 mL stainless steel high pressure reactor having a Pyrex glass liner and a magnetic stir bar was charged with 5 mL of tetrahydrofuran, 0.5 mmol of 1,2,3-trimethylbenzene internal standard, 0.6 mmol of $CH_3OH$, 35.1 mg of $(PPh_3)_2PdCl_2$, and 55.5 mg of N-acetyl-2-pyrroline. The reactor ws pressurized to 1000 psi with CO at room temperature, and the reaction mixture was stirred for 44.25 hours at 100° C. Thereafter, the reactor was cooled to room temperature and vented to atmospheric pressure. The product mixture was analyzed by gas chromatography and mass spectroscopy, and the analysis indicated complete conversion of N-acetyl-2-pyrroline and a 47.9% yield of N-acetylproline methyl ester.

EXAMPLE 30

A 70 mL stainless steel high pressure reactor having a Pyrex glass liner and a magnetic stir bar was charged with 5 mL of tetrahydrofuran, 0.5 mmol of n-pendadecane internal standard, 0.5 mmol of $CH_3OH$, 35.1 mg of $(PPh_3)_2PdCl_2$, and 56.6 mg of N-acetyl-2-pyrroline. The reactor was pressurized to 1000 psi with CO at room temperature, and the reaction mixture was stirred at 100° C. for 26 hours. Thereafter, the reactor was cooled to room temperature and vented to atmospheric pressure. The product mixture was analyzed by gas chromatography, and the analysis indicated 98.4% conversion of N-acetyl-2-pyrroline and 42.8% yield of N-acetylproline methyl ester.

EXAMPLE 31

A 70 mL stainless steel high pressure reactor having a Pyrex glass liner and a magnetic stir bar was charged with 5 mL of tetrahydrofuran, 0.5 mmol of n-pentadecane internal standard, 0.5 mmol of $CH_3OH$, 6.5 mg of $Co_2(CO)_8$, and 54.9 mg of N-acetyl-2-pyrroline. The reactor was pressurized with 1320 psi of CO and 300 psi of $H_2$ at room temperature, and the reaction mixture ws stirred at 100° C. for 22 hours. Thereafter, the reactor was cooled to room temperature and vented to atmospheric pressure. The product mixture was analyzed by gas chromatography, and the analysis indicated 82.3% conversion of N-acetyl-2-pyrroline and 7.6% yield of N-acetylproline methyl ester.

EXAMPLE 32

A 70 mL stainless high pressure reactor having a Pyrex glass liner and a magnetic stir bar was charged with 5 mL of diglyme, 0.5 mmol of n-pentadecane internal standard, 0.5 mmol of $CH_3OH$, 4.0 mg of $Co_2(CO)_8$, 19.6 mg pyridine and 55.5 mg of N-acetyl-2-pyrroline. The reactor was pressurized with 1320 psi of CO and 300 psi of $H_2$ at room temperature, and the reaction mixture was stirred at 100° C. for 22 hours. Thereafter, the reactor was cooled to room temperature and vented to atmospheric pressure. The product mixture was analyzed by gas chromatography, and the analysis indicated 92.2% conversion of N-acetyl-2-pyrroline and 37.3% yield of N-acetylproline methyl ester.

EXAMPLE 33

A 70 ml stainless steel high pressure reactor having a Pyrex glass liner and a magnetic stir bar was charged with 5 mL of tetrahydrofuran, 0.5 mmol of n-pentadecane internal standard, 0.5 mmol of $CH_3OH$, 10.0 mg of $Co_2(CO)_6(PPh_3)_2$, and 55.0 mg of N-acetyl-2-pyrroline. The reactor was pressurized with 1320 psi of CO and 300 psi of $H_2$ at room temperature, and the reaction mixture was stirred at 100° C. for 21.75 hours. Thereafter, the reactor was cooled to room temperature and vented to atmospheric pressure. The product mixture was analyzed by gas chromatography, and the analysis indicated 76.6% conversion of N-acetyl-2-pyrroline and 4.1% yield of N-acetylproline methyl ester.

EXAMPLE 34

A 70 mL stainless steel high pressure reactor having a Pyrex glass liner and a magnetic stir bar was charged with 5 mL of tetrahydrofuran, 0.5 mmol of n-pentadecane internal standard, 0.75 mmol of $CH_3OH$, 56.8 mg of $(PPh_3)_2PdCl_2$, and 72.35 mg of N-acetyl-2-pyrroline. The reactor was pressurized with 1000 psi of CO and 300 psi of $H_2$ at room temperature, and the reaction mixture was stirred at 100° C. for 18 hours. Thereafter, the reactor was cooled to room temperature and vented to atmospheric pressure. The product mixture was analyzed by gas chromatography, and the analysis indicated 100% conversion of N-acetyl-2-pyrroline and 25.2% yield of N-acetylproline methyl ester.

EXAMPLE 35

A 70 mL stainless steel high pressure reactor having a Pyrex glass liner and a magnetic stir bar was charged with 5 mL of tetrahydrofuran, 0.5 mmol of n-pentadecane internal standard, 0.5 mmol of $C_2H_5OH$, 40 mg of $(PPh_3)_2PdCl_2$, and 55.5 mg of N-acetyl-2-pyrroline. The reactor was pressurized to 1000 psi with CO at room temperature, and the reaction mixture was stirred at 100° C. for 21 hours. Thereafter, the reactor was cooled to room temperature and vented to atmospheric pressure. The product mixture was analyzed by gas chromatography and mass spectrometry, and the analysis indicated 100% conversion of N-acetyl-2-pyrroline and 34% yield of N-acetylproline ethyl ester.

EXAMPLE 36

A 70 mL stainless steel high pressure reactor having a Pyrex glass liner and a magnetic stir bar was charged with 5 mL of tetrahydrofuran, 0.5 mmol of n-pentadecane internal standard, 0.5 mmol of 2-propanol, 40 mg of $(PPh_3)_2PdCl_2$, and 55.5 mg of N-acetyl-2-pyrroline. The reactor was pressurized to 1000 psi with CO at room temperature, and the reaction mixture ws stirred at 100° C. for 21 hours. Thereafter, the reactor was cooled to room temperature and vented to atmospheric pressure. The product mixture was analyzed by gas chromatography and mass spectrometry, and the analysis indicated 100% conversion of N-acetyl-2-pyrroline and 23% yield of N-acetylpyrroline 2-propyl ester.

EXAMPLE 37

A 70 mL stainless steel high pressure reactor having a Pyrex glass liner and a magnetic stir bar was charged with 5 mL of tetrahydrofuran, 0.5 mol of n-pentadecane internal standard, 0.5 mmol of tert-butyl alcohol, 40 mg of $(PPh_3)_2PdCl_2$, and 55.5 mg of N-acetyl-2-pyrroline. The reactor was pressurized to 1000 psi with Co at room temperature, and the reaction mixture was stirred at 100° C. for 21 hours. Thereafter, the reactor was cooled to room temperature and vented to atmospheric pressure. The product mixture was analyzed by gas chromatography and mass spectrometry, and the analysis indicated 98.6% conversion of N-acetyl-2-pyrroline and 1.0% yield of N-acetylproline tert-butyl ester.

EXAMPLE 38

A 70 mL stainless steel high pressure reactor having a Pyrex glass liner and a magnetic stir bar was charged with 5 mL of tetrahydrofuran, 0.5 mmol of n-pentadecane internal standard, 0.5 mmol of $CH_3OH$, 4.88 mg of $Fe(CO)_5$, and 57.19 mg of N-acetyl-2-pyrroline. The reactor was pressurized to 1000 psi with CO at room temperature, and the reaction mixture was stirred at 100° C. for 21 hours. Thereafter, the reactor was cooled to room temperature and vented to atmospheric pressure. The product mixture was analyzed by gas chromatography, and the analysis indicated 86.7% conversion of N-acetyl-2-pyrroline and 1.1% yield of N-acetylproline methyl ester.

EXAMPLE 39

A 70 mL stainless steel high pressure reactor having a Pyrex glass liner and a magnetic stir bar was charged with 5 mL of $CH_3OH$, 0.5 mmol of n-pentadecane internal standard, 4.2 mg of $Co_2(CO)_8$, and 33.45 mg of N-acetyl-2-pyrroline. The reactor was pressurized with 1300 psi of CO and 300 psi of $H_2$ at room temperature, and the reaction mixture was stirred at 100° C. until conversion of N-acetyl-2-pyrroline was completed. Thereafter, the reactor was cooled to room temperature and vented to atmospheric pressure. The product mixture was analyzed by gas chromatography, and the analysis indicated 18.1% yield of N-acetylproline methyl ester.

EXAMPLE 40

A 70 mL stainless steel high pressure reactor having a Pyrex glass liner nd a magnetic stir bar was charged with 5 mL of tetrahydrofuran, 0.5 mmol of n-pentadecane internal standard, 0.5 mmol of $CH_3OH$, 45.8 mg of $(PPh_3)_2PdCl_2$, and 53.3 mg of N-acetyl-2-pyrroline. The reactor was pressurized with 700 psi of CO and 300 psi of $H_2$ at room temperature, and the reaction mixture was stirred at 100° C. for 18 hours. Thereafter, the reactor was cooled to room temperature and vented to atmospheric pressure. The product mixture was analyzed by gas chromatography, and the analysis indicated 99.0% conversion of N-acetyl-2-pyrroline. The reactor was pressurized with 700 psi of CO and 300 psi of $H_2$ at room temperature, and the reaction mixture was stirred at 100° C. for 18 hours. Thereafter, the reactor was cooled to room temperature and vented to atmospheric pressure. The product mixture was analyzed by gas chromatography, and the analysis indicated 99.0% conversion of N-acetyl-2-pyrroline and 18.5% yield of N-acetylproline methyl ester.

EXAMPLE 41

A 70 mL stainless steel high pressure reactor having a Pyrex glass liner and a magnetic stir bar was charged with 5 mL of tetrahydrofuran, 0.5 mmol of n-pentadecane internal standard, 1.0 mmol of $CH_3OH$, 82.6 mg of $(PPh_3)_2PdCL_2$, and 107.2 mg of N-acetyl-2-pyrroline. The reactor was pressurized to 1000 psi with CO at room temperature, and the reaction mixture was stirred at 100° C. for 18 hours. Thereafter, the reactor was cooled to room temperature and vented to atmospheric pressure. The product mixture was analyzed by gas chromatography, and the analysis indicated 98.4% conversion of N-acetyl-2-pyrroline and 36.4% yield of N-acetylproline methyl ester.

We claim:

1. A process for making a compound hydrolyzable to an α-amino acid which comprises reacting an enamide with CO and water or an organic hydroxyl compound according to the equation

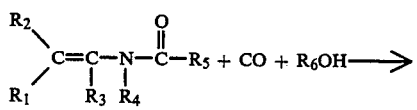

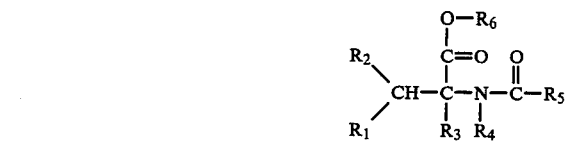

(Hydrocarboxylation product)

wherein each of $R_1$, $R_2$, $R_3$, $R_4$, $R_5$ and $R_6$ contain no ethylenic or acetylenic unsaturation, contain zero to 15 carbon atoms and are independently selected from:

(1) H or a hydrocarbyl group,
(2) a hydrocarbyl group substituted with acylamino, acyl-(N-hydrocarbyl) amino, formylamino and formyl-(N-hydrocarbyl) amino, hydrocarbyloxy, hydrocarbylthio, acyloxy, acylthio, carboxyl, hydrocarbyl carboxyl, hydrocarbyl thiocarboxyl, hydrocarbyl amino, dihydrocarbyl amino, hydrocarbonyl, hydrocarbyl carbonyl, 3-indolyl, carbamoyl, hydrocarbylcarbamoyl, dihydrocarbylcarbamoyl, 5-imidazolyl, 2-guanidinoyl and halo groups, and wherein
(3) $R_1$ and $R_2$ can additionally be selected independently from acylamino, acyl-(N-hydrocarbyl) amino, formylamino and formyl-(N-hydrocarbyl) amino, hydrocarbyloxy, hydrocarbylthio, hydrocarbyl amino, dihydrocarbyl amino, acyloxy, acylthio, carboxyl, hydrocarbyl carboxyl, hydrocarbyl thiocarboxyl, hydrocarbonyl, hydrocarbyl carbonyl, 3-indolyl, carbamoyl, hydrocarbyl carbamoyl, dihydrocarbylcarbamoyl, 5-imidazolyl, 2-guanidinoyl and halo groups, and wherein $R_6$ can additionally be a hydrocarbyl group having one or more hydroxy substituents, and wherein $R_4$ is linked with $R_1$ or $R_2$ to form or complete a ring.

2. A process according to claim 1, with the added step of making an amino acid of the formula

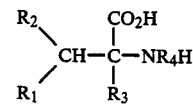

by hydrolyzing a hydrocarboxylation product of claim 1.

* * * * *